(12) United States Patent
Shida et al.

(10) Patent No.: US 7,074,946 B2
(45) Date of Patent: Jul. 11, 2006

(54) METHOD OF PRODUCING GLYCIDYL 2-HYDROXYISOBUTYRATE

(75) Inventors: Takatoshi Shida, Niigata (JP); Syu Suzuki, Niigata (JP)

(73) Assignee: Mitsubishi Gas Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/001,780

(22) Filed: Dec. 1, 2004

(65) Prior Publication Data

US 2005/0119496 A1    Jun. 2, 2005

(30) Foreign Application Priority Data

Dec. 2, 2003    (JP)    ............... 2003-403073

(51) Int. Cl.
*C07D 301/30*    (2006.01)

(52) U.S. Cl. ..................... 549/515; 549/557

(58) Field of Classification Search ............... 549/515, 549/557

See application file for complete search history.

(56) References Cited

U.S. PATENT DOCUMENTS 2,772,296 A    11/1956    Mueller 5,168,110 A * 12/1992 Van Den Elshout et al. ..... 525/438

FOREIGN PATENT DOCUMENTS

| EP | 0 761 660 A1 | 3/1997 |
| GB | 648 959 A1 | 1/1951 |
| JP | 5-32650 | 2/1993 |
| JP | 9-59268 | 3/1997 |

OTHER PUBLICATIONS

Patent Abstracts of Japan for JP5-32650 published on Feb. 9, 1993.
Patent Abstracts of Japan for JP9-59268 published on Mar. 4, 1997.
Macchia, B., et al., "Role of the (Acyloxy) methyl Moiety in Eliciting the Adrenergic β-Blocking Activity of 3-(Acyloxy) propanolamines[1]", J. Med. Chem., 1987, vol. 30, pp. 616-622.

* cited by examiner

*Primary Examiner*—Bernard Dentz
(74) *Attorney, Agent, or Firm*—Darby & Darby

(57) ABSTRACT

A method of stably producing glycidyl 2-hydroxyisobutyrate at high purity and high yield is provided. A reactive diluent is provided for an epoxy resin including the above-mentioned glycidyl 2-hydroxyisobutyrate, and an epoxy resin composition.

5 Claims, No Drawings

METHOD OF PRODUCING GLYCIDYL 2-HYDROXYISOBUTYRATE

INCORPORATION BY REFERENCE

The present application claims priority under 35 U.S.C. §119 to Japanese Patent Application No. 2003-403073 filed on Dec. 2, 2003. The content of the application is incorporated herein by reference in its entirety.

TECHNICAL FIELD OF THE INVENTION

The present invention relates to a method of producing glycidyl 2-hydroxyisobutyrate of the formula (2):

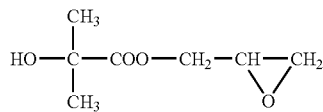

(2)

More particularly, the present invention relates to a method of producing glycidyl 2-hydroxyisobutyrate at high purity by reacting a raw material compound in the presence of water, and a reactive diluent for epoxy resin comprising glycidyl 2-hydroxyisobutyrate obtained by the above-mentioned method and, an epoxy resin composition.

BACKGROUND OF THE INVENITON

Methods of producing a glycidyl ester from a carboxylic acid or its alkali metal salt and epichlorohydrin using a catalyst such as a quaternary ammonium salt and the like are known (see, for example, Japanese Patent Application Laid-Open (JP-A) Nos. 9-59268 and 2003-171371). Also, methods of producing a glycidyl ether from alcohol and epichlorohydrin are known (see, for example, JP-A Nos. 5-32650 and 5-163260).

However, since both a hydroxyl group and a carboxyl group easily react with epichlorohydrin, methods of easily and stably producing a compound having a hydroxyl group and a glycidyl group in the same molecule at high purity have not been found yet.

SUMMARY OF THE INVENTION

If a compound as represented by the above-mentioned formula (2) having a plurality of characteristic reactive groups is easily and stably produced at high purity, various applications such as use as a reactive diluent can be expected. Then, the present invention has an objective of providing a method of producing glycidyl 2-hydroxyisobutyrate at high purity.

The present inventors have intensively studied, and resultantly found a method of suppressing the selectivity of a reaction of a tertiary hydroxyl group into a glycidyl ether and selectively converting a carboxylic acid or its alkali metal salt compound into a glycidyl ester by conducting the reaction under specific conditions, leading to completion of the present invention.

Namely, the present invention is as described below.
1. A method of producing glycidyl 2-hydroxyisobutyrate of the formula (2):

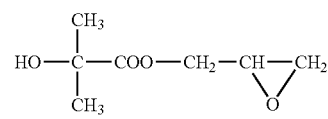

(2)

wherein a raw material compound of the formula (1):

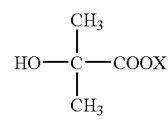

(1)

[wherein X in the formula (1) represents an alkali metal atom or a hydrogen atom] is reacted with epichlorohydrin in the presence of a catalyst, characterized in that the reaction is conducted in the presence of water in the reaction system.
2. The method of producing glycidyl 2-hydroxyisobutyrate according to the above-mentioned item 1, wherein the amount of water present in the reaction system is in the range of 0.3 wt % to 2.5 wt %.
3. The method of producing glycidyl 2-hydroxyisobutyrate according to the above-mentioned item 1, wherein the amount of water present in the reaction system is controlled in the range of 0.3 wt % to 2.5 wt % by adding water at the time of charging raw materials.
4. The method of producing glycidyl 2-hydroxyisobutyrate according to the above-mentioned item 1, wherein X in the raw material compound of the formula (1) is Na, K or Li.
5. The method of producing glycidyl 2-hydroxyisobutyrate according to the above-mentioned item 1, wherein the catalyst is a quaternary ammonium salt or an alkali metal halide.
6. The method of producing glycidyl 2-hydroxyisobutyrate according to the above-mentioned item 1, wherein the raw material compound of the formula (1) and epichlorohydrin are reacted at a charging molar ratio (raw material compound of the formula (1): epichlorohydrin) of 1:2 to 1:10, at a reaction temperature of 80° C. to 125° C. for 0.5 to 5 hours.
7. A reactive diluent for an epoxy resin, comprising glycidyl 2-hydroxyisobutyrate obtained by the method according to the above-mentioned item 1.
8. An epoxy resin composition, comprising the reactive diluent according to the above-mentioned item 7.

BEST MODE FOR CARRYING OUT THE INVENTION

The present invention will be illustrated below.
The present invention is a method of producing glycidyl 2-hydroxyisobutyrate of the formula (2), wherein a carboxylic acid of the formula (1) or its alkali metal salt compound is reacted with epichlorohydrin in the presence of a catalyst, characterized in that the reaction is conducted in the presence of water in the reaction system.
By using the method of the present invention, the reaction yield of glycidyl 2-hydroxyisobutyrate can be enhanced. The side reaction can be suppressed and the amount of by-products having a boiling point near that of the intended compound can be decreased. By this, the intended compound can be purified more easily by distillation under reduced pressure. Thus, by the presence of water in the reaction system, the reaction yield of the intended glycidyl ester is improved, simultaneously, the amount of by-products (having boiling point near that of glycidyl 2-hydroxyisobutyrate) which cannot easily be separated in purification by distillation can be reduced and the purity of the resulting product can be increased. Therefore, glycidyl 2-hydroxyisobutyrate can be easily and stably produced at high purity.

The raw material used in the present invention is a compound having a hydroxyl group and a carboxyl group in the molecule or its alkali metal salt as shown in the formula (1). X in the formula (1) represents an alkali metal atom or a hydrogen atom. Preferred examples of the alkali metal are sodium, potassium and lithium. In particular, alkali metal salts wherein X in the formula (1) represents sodium, potassium or the like are more preferable as a raw material. A compound of the formula (1) is known or can be synthesized easily according to an ordinary method.

Epichlorohydrin is known and can be synthesized easily according to an ordinary method. As the raw material compound used in the present invention, commercially available products can also be used.

The charging molar ratio of a raw material compound of the formula (1) and epichlorohydrin (raw material compound of the formula (1): epichlorohydrin) is desirably in the range of 1:2 to 1:10. More desirably, this range is 1:2.5 to 1:9, particularly desirably 1:3 to 1:8. When the charging molar ratio of epichlorohydrin is smaller than 1:2, the reaction yield lowers undesirably. When the charging molar ratio of epichlorohydrin exceeds 1:10, removal of surplus epichlorohydrin after completion of the reaction takes a longer time, and this ratio is not desirable also from the standpoint of cost.

This reaction is conducted in the presence of a catalyst. Specifically, use of quaternary ammonium salts such as tetramethylammonium chloride, tetraethylammonium chloride and the like, halogenated alkali metal salts such as sodium iodide, sodium bromide and the like is desirable. These catalysts can be used singly or in combination of two or more. Though the use amount of a catalyst is not particularly limited, usually, the range of 10 ppm to 20 wt %, preferably of 0.05 wt % to 5 wt % based on a raw material compound of the formula (1) is desirable. If necessary, organic solvents such as benzene, toluene, xylene, N,N-dimethylformamide, dimethyl sulfoxide and the like may also be used.

The amount of water to be present in the reaction system is preferably in the range of 0.3 to 2.5 wt %, more preferably of 0.3 to 1.5 wt %. The amount of water in the reaction system is controlled by adding water in the reaction system. When the amount of water in the reaction system is less than 0.3 wt %, an effect of suppressing by-products having a boiling point near that of the intended compound is not sufficiently obtained in some cases. When the amount of water in the reaction system exceeds 2.5 wt %, there is a tendency that the amount of by-products other than the above-mentioned compounds increases and the reaction yield lowers. The amount of water in the present invention is calculated based on the following formula:

Water amount( wt %)=$d \div (a+b+c+d) \times 100$ where
a: weight of raw material compound of the formula (1)
b: weight of epichlorohydrin
c: weight of catalyst
d: weight of water added The reaction can be conducted under reduced pressure or pressurized conditions as far as stirring is not disturbed under solid-liquid suspended condition. From the standpoint of cost, the reaction under atmospheric pressure may be more preferable. The reaction temperature is desirably in the range of 80 to 125° C. When the reaction temperature is 80° C. or less, the reaction rate lowers undesirably, and when over 125° C., boiling and evaporation of epichlorohydrin become intense and the reaction yield lowers. Time required for the reaction is preferably 0.5 to 5 hours. More preferably, the reaction is performed for a time in the range of 0.75 to 1.5 hours. When the reaction time is less than 0.5 hours, progress of the reaction may be undesirably insufficient. A reaction time of 5 hours or more may increase the amount of by-products and also may lower the production amount per unit time, being undesirable from the standpoint of cost.

After completion of the reaction, the intended compound glycidyl 2-hydroxyisobutyrate can be separated and obtained according to ordinary methods such as filtration, distillation, extraction and the like. For example, water is added to mixed liquid after the reaction and they are mixed by stirring. Then, an organic solvent phase containing glycidyl 2-hydroxyisobutyrate is separated, and a solvent is distilled off, to obtain the intended glycidyl 2-hydroxyisobutyrate. The obtained glycidyl 2-hydroxyisobutyrate can be subjected, if necessary, to known methods such as distillation under reduced pressure, column chromatography and the like, to further increase its purity.

A glycidyl ester obtained by the method of the present invention, i.e. glycidyl 2-hydroxyisobutyrate, can be used as a reactive diluent for epoxy resin. When the glycidyl ester is used as a reactive diluent, it can be used singly or as a mixture with other reactive diluent. When the glycidyl ester is used as a mixture with other reactive diluent, a blend ratio of the mixture is not particularly limited, however, it is desirable that the glycidyl ester is contained in an amount of 30 wt % or more, more preferably 50 wt % or more, further preferably 70 wt % or more, particularly preferably 90 wt % or more based on the total amount of the reactive diluent. When the content of the glycidyl ester is less than 30 wt %, the property as a reactive diluent may lower and the diluent cannot be used simply. As the reactive diluent, generally known reactive diluents for epoxy resin and the like can also be used in addition to the above-mentioned glycidyl ester.

The epoxy resin composition of the present invention comprises the above-mentioned reactive diluent in addition to an epoxy resin and a hardener.

The epoxy resin is a resin having at least two epoxy groups in the molecule, and examples thereof include bisphenol A type epoxy resins, bisphenol F type epoxy resins and bisphenol S type epoxy resins obtained by a polymerization reaction of an epihalohydrin with bisphenol such as bisphenol A, bisphenol F, bisphenol S and the like, further, epoxy resins obtained by a polymerization reaction of an epihalohydrin with 4,4'-dihydroxybiphenyl, dihydroxynaphthalene and the like, (poly)ethylene glycol diglycidyl ether, (poly)propylene glycol diglycidyl ether, 1,6-hexanediol diglycidyl ether, cyclohexanedimethanol diglycidyl ether, neopentyl glycol diglycidyl ether, polyoxyalkylene glycol diglycidyl ether, polyglycidyl ether of glycerins, novolak-epoxy resins obtained by a polymerization reaction of an epihalohydrin with a novolak resin polymerized substance, and the like. These epoxy resins can be used singly or in combination of two or more.

As the hardener, any substances can be used as far as the substance can react with the epoxy resin as described above, and with the glycidyl ester as a reactive diluent obtained by the method of the present invention. Examples thereof include anhydrides such as hexahydrophthalic anhydride, tetrahydrophthalic anhydride, phthalic anhydride, methylhexahydrophthalic anhydride, methyltetrahydrophthalic anhydride, methyl nadic anhydride, trimellitic anhydride and the like, amines such as isophoronediamine, ethylenediamine, diethylenetriamine, triethylenetetramine, phenylenediamine, xylylenediamine, bis(aminomethyl)cyclohexane, dicyanediamide and the like and modified substances thereof, amine-based epoxy resin adducts, polyamide, so-called Mannich type amine-based hardeners obtained by condensation of an amine, phenol and formalin, phenol-based hardners, catalyst-based hardners and the like. These hardeners can be used singly or in combination of two or more.

In the epoxy resin composition of the present invention, the compounding ratio of an epoxy resin component and a diluent component containing the glycidyl ester is preferably 60:40 to 95:5 by weight. When the amount of the epoxy resin component is larger than the above-mentioned proportion, decrease in viscosity does not occur sufficiently, and when the amount of the epoxy resin component is smaller than the above-mentioned proportion, the heat resistance and mechanical property of a hardened substance lower due to decrease in cross-linking density.

In the epoxy resin composition of the present invention, the amount of a hardener component to be compounded is not particularly limited as far as the property of an epoxy resin cured product is sufficiently obtained. For example, in the case of amine-based hardner, it is desirable that a hardener component is mixed in a compounding ratio of 0.5 to 1.5 equivalents based on the equivalent of epoxy groups in the epoxy resin component and the diluent component in total. In the above-mentioned hardener component, a primary amino group and secondary amino group act as 2 equivalents and 1 equivalent, respectively.

In the epoxy resin composition of the present invention, inorganic fillers such as silica, titanium oxide, calcium carbonate and the like, and hardening accelerators such as imidazole and its derivatives, benzyldimethylamine and the like, can be used, if necessary. Additives such as solvents, diluents, fillers, flame retardants, releasing agents, coloring agents and the like can also be added, if necessary.

EXAMPLES

The present invention will be specifically illustrated with reference to examples and comparative examples, however, the scope of the invention is not limited to these examples at all. In Tables, epichlorohydrin is abbreviated to EpCH, glycidyl 2-hydroxyisobutyrate is abbreviated to GHIB, and tetramethylammonium chloride is abbreviated to TMAC.

Examples 1 to 5 and Comparative Example 1

Into a 200 mL three-necked flask equipped with a stirrer and reflux tube was charged 37.83 g (0.3 mol) of sodium 2-hydroxyisobutyrate, 138.7 g (1.5 mol) of epichlorohydrin, 0.25 g of tetramethylammonium chloride and pure water at room temperature under normal pressure, and heated at temperatures from room temperature to an inner temperature of 120° C. over a period of 10 minutes, then, reacted while keeping this temperature for 1.5 hours, then, cooled to room temperature. To this was added water and allowed to stand for 1.5 hours, then, an organic solvent phase was removed. After epichlorohydrin was distilled off in a distillation apparatus equipped with a Vigreux distilling column, the obtained residual liquid was distilled under reduced pressure to obtain glycidyl 2-hydroxyisobutyrate. The charging molar ratio, reaction conditions and reaction yield, and the amount of by-products after distillation under reduced pressure are shown in Tables 1 and 2. The addition ratio of catalysts and water in the tables were calculated based on the total weight of a raw material compound of the formula (1), epichlorohydrin, catalyst and water.

TABLE 1

| | | Example 1 | Example 2 | Example 3 |
|---|---|---|---|---|
| Charging molar ratio (raw material compound (1)/EpOH) | | 0.2 | 0.2 | 0.2 |
| Reaction temperature (° C.) | | 120 | 120 | 120 |
| Reaction time (hr) | | 1.5 | 1.5 | 1.5 |
| Catalyst | kind | TMAC | TMAC | TMAC |
| | addition amount (g) | 0.25 | 0.25 | 0.25 |
| | addition ratio (wt %) | 0.14 | 0.14 | 0.14 |
| Water | addition amount (g) | 0.55 | 1.00 | 2.00 |
| | addition ratio (wt %) | 0.31 | 0.56 | 1.11 |
| Reaction yield (%) | | 69 | 66 | 65 |
| Amount of by-product (wt %) | | 2.1 | 0.70 | 0.30 |

TABLE 2

| | | Example 4 | Example 5 | Comparative Example 1 |
|---|---|---|---|---|
| Charging molar ratio (raw material compound (1)/EpOH) | | 0.2 | 0.2 | 0.2 |
| Reaction temperature (° C.) | | 120 | 120 | 120 |
| Reaction time (hr) | | 1.5 | 1.5 | 1.5 |
| Catalyst | kind | TMAC | TMAC | TMAC |
| | addition amount (g) | 0.25 | 0.25 | 0.25 |
| | addition ratio (wt %) | 0.14 | 0.14 | 0.14 |
| Water | addition amount (g) | 0.20 | 5.00 | 0 |
| | addition ratio (wt %) | 0.11 | 2.75 | 0 |
| Reaction yield (%) | | 62 | 47 | 62 |
| Amount of by-product (wt %) | | 4.9 | 0.85 | 6.4 |

As shown in Tables 1 and 2, under the conditions according to the present invention (Examples 1 to 5), the reaction yield was high, and the amount of by-products after distillation under reduced pressure was suppressed to low. These effects are remarkable when the addition amount of water was controlled in a specific range (Examples 1 to 3). In contrast, under conditions out of the range according to the present invention (Comparative Example 1), it is evident that the amount of by-products after distillation under reduced pressure was large, and the intended glycidyl 2-hydroxyisobutyrate was not obtained efficiently.

Example 6

The performance as a reactive diluent of glycidyl 2-hydroxyisobutyrate obtained according to the method of the above-mentioned example (colorless liquid, boiling point: 97° C./0.7 kPa) was tested. As a control, glycidyl neodecanoate (manufactured by Japan Epoxy Resin, Cardula E10) which is a commercially available glycidyl ester was used. The physical properties of the prepared epoxy resin composition and a coating film formed by using this are shown in Table 3. Measurement and test methods for evaluation were conducted according to methods described below.

Here, the addition amount of a reactive diluent is based on the total weight of an epoxy resin and reactive diluent.

(1) Viscosity Measurement

To a main agent bisphenol A type liquid epoxy resin (manufactured by Japan Epoxy Resin, Epikote 828) was added 5 wt % of a reactive diluent, and the viscosity at 25° C. was measured by a B type viscometer, and the viscosity ratio after addition {(viscosity in adding diluent/viscosity of only main agent)×100%} was calculated.

(2) Production of Coating Film

To a main agent bisphenol A type liquid epoxy resin (Epikote 828) was added 5 wt % of a reactive diluent, and a coating film having a thickness of 200 μm was produced by an ordinary method using as a hardener an isophorone diamine adduct of a bisphenol A type liquid epoxy resin.

(3) Evaluation of Curing Property

To a main agent bisphenol A type liquid epoxy resin (Epikote 828) was added 5 wt % of a reactive diluent. A time until complete drying was measured by an RCI drying meter.

TABLE 3

| Composition of paint liquid and physical property of coating film | Present glycidyl ester | Control article |
|---|---|---|
| Epikote 828 (wt %) | 70.5 | 70.5 |
| GHIB (wt %) | 3.7 | |
| Cardura E10 (wt %) | | 3.7 |
| Hardener (wt %) | 25.8 | 25.8 |
| Viscosity ratio after addition (%) | 40 | 45 |
| Curing property (dry through) | 9.25 | 18.5 |

Hardener: To 100 parts by weight of an adduct obtained by reacting Epikote 828 and isophorone diamine at a molar ratio of 1:8 was added 10 parts by weight of benzyl alcohol and the obtained product was used.

As shown in Table 3, this glycidyl ester (glycidyl 2-hydroxyisobutyrate) showed a decrease in viscosity after addition of 40% in contrast to 45% of a control article, showing high dilution effect. Further, the curing property was 9.25 hours, showing significant increase in rate in contrast to that (18.5 hours) of a control article. Thus, it is found that glycidyl 2-hydroxyisobutyrate is useful as a reactive diluent for epoxy resin.

INDUSTRIAL APPLICABILITY

Glycidyl 2-hydroxyisobutyrate produced by the method of the present invention is useful as a reactive diluent, and an epoxy resin composition comprising this reactive diluent is suitably used for civil engineering and construction materials, and embedding, casting, adhesion, painting, lamination and the like of electric and electronic parts.

What is claimed is:

1. A method of producing glycidyl 2-hydroxyisobutyrate of the formula (2):

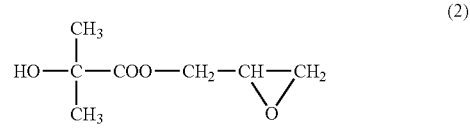

wherein a raw material compound of the formula (1):

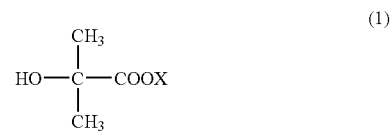

wherein X in the formula (1) represents an alkali metal atom or a hydrogen atom
is reacted with epichlorohydrin in the presence of a catalyst, characterized in that the reaction is conducted in the presence of water in the reaction system, wherein the amount of water present in the reaction system is controlled in the range of 0.3 wt % to 2.5 wt %.

2. The method of producing glycidyl 2-hydroxyisobutyrate according to claim 1, wherein the amount of water present in the reaction system is controlled in the range of 0.3 wt % to 2.5 wt % by adding water at the time of charging raw materials.

3. The method of producing glycidyl 2-hydroxyisobutyrate according to claim 1, wherein X in the raw material compound of the formula (1) is Na, K or Li.

4. The method of producing glycidyl 2-hydroxyisobutyrate according to claim 1, wherein the catalyst is a quaternary ammonium salt or an alkali metal halide.

5. The method of producing glycidyl 2-hydroxyisobutyrate according to claim 1, wherein the raw material compound of the formula (1) and epichlorohydrin are reacted at a charging molar ratio (raw material compound of the formula (1):epichlorohydrin) of 1:2 to 1:10, at a reaction temperature of 80° C. to 125° C. for 0.5 to 5 hours.

* * * * *

UNITED STATES PATENT AND TRADEMARK OFFICE
CERTIFICATE OF CORRECTION

PATENT NO.       : 7,074,946 B2
APPLICATION NO.  : 11/001780
DATED            : July 11, 2006
INVENTOR(S)      : Takatoshi Shida et al.

It is certified that error appears in the above-identified patent and that said Letters Patent is hereby corrected as shown below:

Title page, item [73] Assignee:

Delete "Mitsubishi Gas Chemical Co., Ltd., Tokyo (JP)" and substitute -- Mitsubishi Gas Chemical Co., Inc., Tokyo (JP) --.

Signed and Sealed this

Twenty-seventh Day of March, 2007

JON W. DUDAS
*Director of the United States Patent and Trademark Office*